United States Patent [19]

Gatturna

[11] Patent Number: 5,011,473
[45] Date of Patent: Apr. 30, 1991

[54] DEVICE FOR SECURING AND POSITIONING A WIRE TO A NEEDLE

[75] Inventor: Roland F. Gatturna, Walpole, Mass.

[73] Assignee: Mitek Surgical Products Inc., Dedam, Mass.

[21] Appl. No.: 362,013

[22] Filed: Jun. 6, 1989

[51] Int. Cl.$^5$ ............................................. A61M 31/00
[52] U.S. Cl. ..................................... 604/51; 604/164; 128/754
[58] Field of Search ................. 128/630, 653, 51, 772, 128/657, 754; 604/51, 164–169, 283

[56] References Cited

U.S. PATENT DOCUMENTS

| | | | |
|---|---|---|---|
| 4,349,023 | 9/1982 | Gross | 604/164 |
| 4,378,810 | 4/1983 | Ishizaki et al. | 128/754 |
| 4,616,656 | 10/1986 | Nicholson et al. | 128/630 |
| 4,650,472 | 3/1987 | Bates | 604/158 |
| 4,721,506 | 1/1988 | Teves | 604/51 |

Primary Examiner—Robert A. Hafer
Assistant Examiner—Kerry Owens

[57] ABSTRACT

A wire probe unit having stabilizer with a clamp and a mating cap for locking and precisely positioning a memory probe wire relative to a needle cannula having a hub with a socket at one end and a beveled point at the other end. The clamp has a guide post extending from one end thereof and a set of clamping fingers extending from an opposite end thereof. The guide post is configured to be received within the socket of the hub and the fingers are configured to captively hold the probe wire which is fed through a central bore in the stabilizer and needle cannula. The clamping fingers have tapered ends which fit into a fustro conical socket formed internally of the cap. When the stabilizer is in a retracted position, the probe wire is sheathed in the cannula needle and when the stabilizer is in its forward position, a J-shaped hook at the end of the probe wire extends outwardly from the tip of the needle a predetermined distance.

14 Claims, 1 Drawing Sheet

DEVICE FOR SECURING AND POSITIONING A WIRE TO A NEEDLE

BACKGROUND OF THE INVENTION

1. Field of the Invention

The present invention relates to needle wire localizers for marking lesion locations within a body using a probe wire that is slidably received in a cannula needle and, more particularly, is directed toward a locking and positioning device for a needle wire localizer that constrains and precisely positions a probe wire relative to the cannula needle.

2. Description of the Prior Art

It is known to rely on mammography in conjunction with a cannula needle having a probe wire therein for localization of a presymptomatic, non-palpable breast lesion. In such a procedure, a cannula needle having a wire sheathed therein is inserted so that the pointed end of the needle is located in the tissue area of pathological alteration, preferably, less than 2 cm from the lesion. A mammogram is taken to confirm the probe position. If the probe is not positioned close to the lesion, then the probe is relocated, or an additional probe is inserted, and a further mammogram is taken. When the probe location is acceptable, the cannula needle is taped to the patient and the patient transferred to surgery for lesion excision.

U.S. Pat. No. 4,616,656 and the references cited therein show various medical devices for inserting wires into patients. U.S. Pat. No. 4,616,656 discloses a self-actuating breast lesion probe which utilizes a memory alloy probe wire having a J-bend at its pointed or working end. The probe wire is slidably received within a cannula needle and a locking device having a clamping screw is used to clamp the wire. The end of the screw bears against the wire and prevents it from moving relative to the needle. The locking device of this patent suffers from the disadvantage that the screw causes an undesirable bend in the wire.

SUMMARY OF THE INVENTION

It is an object of the present invention to provide a positive locking and positioning device for a needle wire localizer for precisely marking the location of a lesion within a body by means of a probe wire.

It is another object of the present invention to provide a positive locking and positioning device for a needle wire localizer that utilizes a probe wire with J-curved tip for localizing a lesion within a body.

It is a further object of the invention to provide a stabilizer for clamping a probe wire with a J-curved tip that is sheathed in a cannula needle while the cannula needle is inserted into a breast for marking the location of a presymptomatic, non-palpable breast lesion and for extending the wire a precise distance from the end of the needle to mark the location of the lesion.

Yet another object of the invention is to provide a wire probe unit comprising a stabilizer, cannula needle and probe wire for locating a lesion. The cannula needle has a beveled point at one end and a hub with an internal socket at the other end. The stabilizer of the present invention includes a clamp and a mating cap. The clamp has a guide post extending from one end thereof and a set of clamping fingers extending from an opposite end. The guide post is configured to be received within the internal socket of the hub and the fingers are configured to captively hold a memory alloy probe wire having a J-curved tip at a working end. The clamping fingers are tapered inwardly at their ends to form a fustro conical member which is configured to be received in a mating fustro conical chamber formed internally of the cap. The clamp has a threaded section adjacent the fingers and the cap has an internally threaded section that is configured to be turned onto the threaded section of the clamp. The cannula needle, clamp and cap are provided with a central bore that is configured to slidably receive the probe wire.

Initially, the probe wire is inserted into the cannula needle until the J-curved tip abuts the point of the needle. Next, the clamp is fitted on the wire and slid down the probe wire until the guide post rests in the socket in the hub of the needle. The cap is slipped onto the probe wire and slid down the probe wire until it strikes the clamp. As the cap is turned onto the clamp, the clamping fingers bear against the fustro conical chamber and, in turn, they are forced against the probe wire so that the probe wire is fixed against movement relative to the stabilizer. The stabilizer is pulled away from the hub of the needle to its retracted position, withdrawing the wire into the cannula. The cannula needle is ready to be inserted into the breast. After the needle has been inserted into the breast and located at the desired position, the stabilizer is pushed forwardly until the guide post is seated in the socket of the hub. The J-curved tip of the probe wire extends outwardly from the beveled tip of the needle the previously set distance and is anchored within the breast at the site of the lesion.

The invention accordingly comprises the devices, together with their parts, elements and interrelationships that are exemplified in the following disclosure, the scope of which will be indicated in the appended claims.

BRIEF DESCRIPTION OF THE DRAWINGS

A further understanding of the nature and objects of the present invention will become apparent upon consideration of the following detailed description taken in connection with the accompanying drawings, wherein.

DETAILED DESCRIPTION OF THE PREFERRED EMBODIMENTS

Figure 1:
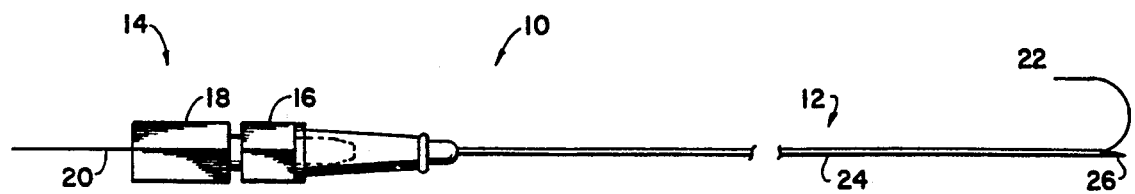
FIG. 1 is a side view of a needle wire localizer having a stabilizer embodying the present invention, the stabilizer being in its closed position and a probe wire extending from a cannula needle.
Figure 2:
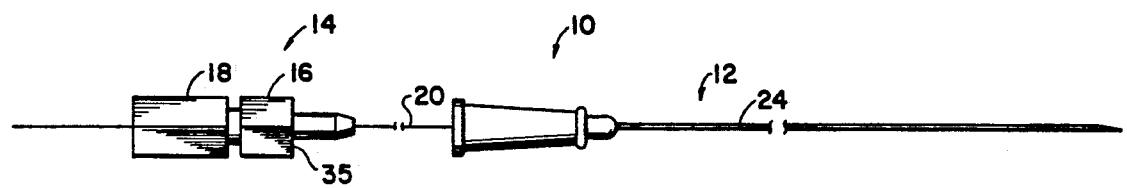
FIG. 2 is a side view of the needle wire localizer with the stabilizer in its retracted position and the probe wire withdrawn into the cannula needle.
Figure 4:
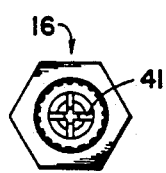
FIG. 4 is an end view of the clamp of FIG. 3 looking from the left side of FIG. 3.

Referring now to the drawings, particularly FIGS. 1 and 2, there is shown a needle wire localizer or wire probe unit 10 comprising a cannula needle 12 and a stabilizer 14 which are configured to receive a probe wire 20. In FIG. 1, stabilizer 14 is in its closed position and probe wire 20 extends from the working end of the cannula needle 12. In FIG. 2, stabilizer 14 is shown in its retracted or opened position and the probe wire 20 is withdrawn into or sheathed in cannula needle 12. As hereinafter described, stabilizer 14 includes a clamp 16 and cap 18 which cooperate to captively hold probe wire 20 so that when the stabilizer is in its closed position, a J-shaped hook 22 at the end of probe wire 20 extends outwardly from a sharp pointed end 26 of cannula needle 12.

Figure 7:
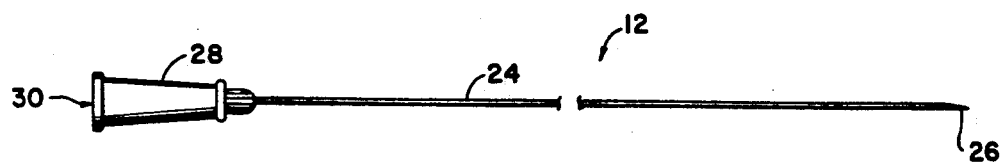
FIG. 7 is a side view of the cannula needle.

As shown in FIG. 7, cannula needle 12 includes a hollow needle 24 having beveled point 26 at a front end and a hub 28 at its back end. Hub 28 is formed with an opened ended socket 30 at its back end.

Figure 3:
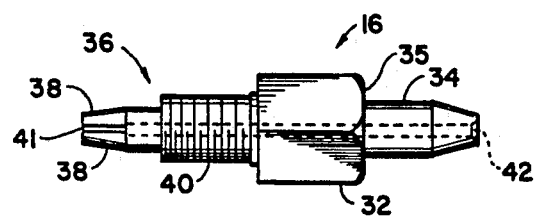
FIG. 3 is a side view of the clamp of the stabilizer of FIG. 1.

As best shown in FIG. 3, clamp 16 includes a medial body 32, a projecting guide 34, and a clamping member 36. In the illustrated embodiment, by way of example, body 32 is a hexagonally shaped member that defines a purchase for holding clamp 16 and for moving probe wire 20. Guide 34, for example, a tapered cylindrical pin which is sized and shaped to fit into socket 30 extends longitudinally from one side of body 32. The end of body 32, which is adjacent guide 34, defines a stop 35 which abuts the end of hub 28 when pin 34 is fully received within the socket.

Clamping member 36 extends longitudinally from the side of body 32 which is opposite guide 34. Clamping member includes a plurality of clamping fingers 38 and an external threaded portion 40 disposed between fingers 38 and body 32. The outer surfaces of fingers 38 tapper inwardly to define a substantially fustro conical structure. In the illustrated example, by way of example, there are four fingers 38, adjacent fingers being separated by a longitudinal slot 41. In an alternate embodiment, the number of fingers is other than four, for example, three or two. In the preferred embodiment, by way of example, clamping member 36 is composed of a plastic such as polycarbonate or a metal such as stainless steel. A central bore 42, which extends longitudinally through clamp 16, is sized and shaped to freely receive probe wire 20 when finger 38 are not in their clamping position and to captively hold the probe wire when the fingers are in their clamping position.

Figure 5:
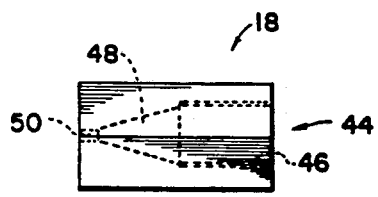
FIG. 5 is a side view of the mating cap of the stabilizer of FIG. 1.
Figure 6:
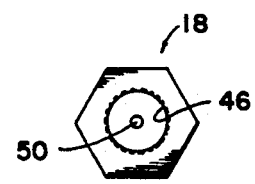
FIG. 6 is an end view of the cap of FIG. 5 looking from the right side of FIG. 5.

As best shown FIG. 5, cap 18 has an internal chamber 44 with an enlarged bore 46 that is internally threaded and terminates in an interior fustro conical chamber 48 which is configured to receive fingers 38. A central bore 50, which is sized to receive probe wire 20, extends longitudinally through cap 18. Internally threaded bore 46 is sized to be threaded onto threaded portion 40 of clamp 16. When cap 18 is turned onto threaded portion 40, fingers 38 are pressed inwardly to their clamping position by fustro conical chamber 48 and they bear against probe wire 20 which is disposed in bore 42. As shown in FIG. 6, by way of example, cap 18 has a hexagonal shape that defines a purchase for holding the cap and for moving probe wire 20 when it is captively held by clamp 16. In the preferred embodiment, by way of example, cap 18 is composed of a plastic such as polycarbonate or a metal such as stainless steel.

In operation of wire probe unit 10, the straight end of probe wire 20 is inserted through needle 24 until the end of the probe wire exits hub 28 and the inner end of J-shaped hook 22 abuts point 26. It is to be noted that J-shaped hook 22 is positioned at the inner most beveled edge of point 26. Next, clamp 16 is placed on probe wire 20 and slid down the probe wire until guide 34 is fully received or seated in socket 30 and stop 35 abuts hub 28, the probe wire being received in bore 42.

Next, cap 18 is place on probe wire 20 and slid down the probe wire until it engages clamp 16, the probe wire being received in bore 50. Clamp 16 is held in place and cap 18 is threaded thereon. As cap 18 is turned onto clamp 16, clamping fingers 38 are pressed against probe wire 20 by the vise-like clamping action caused by the tapered ends of the clamping fingers bearing against the sides of conical chamber 48. Probe wire 20 is clamped against relative movement with respect to stabilizer 14 by the clamping action of clamping fingers 38 on the probe wire. Stabilizer 14 is then moved to its retracted position shown in FIG. 2, and probe unit 10 is ready for use in marking the location of a lesion.

Alternately, clamp 16 and cap 18 are loosely assembled and slid down probe wire 20 as a unit until guide 34 is seated in socket 30 and stop 35 abuts hub 28. Then, cap 18 is turned onto clamp 16 and clamping fingers 38 grip probe wire 20.

The probe wire 20 is preferably manufactured of a material having the memory characteristic of a relatively small curl or hook at its freed distal end. Materials broadly possessing such a memory characteristic and suitable for use in probe unit 10 are, titanium or titanium alloy materials, for example, a nickle titanium alloy. The probe wire 20 could also be formed of a bimetal material that is normally straight but is responsive to body heat for actuation to the hook formation. In any event, probe wire 20 is strong enough to prevent accidental dislodgement and breaking, and is tough to cut. Probe wire 20 has an additional and critical characteristic of being flexibly soft and responsive to manual urging whereby the anchored distal end will release and easily slide from its grasp of tissue and retract into its fully sheathed location within cannula needle 12 without further tissue damage.

As shown in FIG. 2, the probe wire 20 lies straight when sheathed in cannula needle 12. With probe wire 20 in this position, needle 24 is inserted into the body tissue to a location where the pointed end 26 lies at about 2 cm from the lesion as previously determined by a mammography. A mammographic determination is made to confirm accuracy of the anchored distal end of the probe wire to less than 2 cm from the lesion site. If the desired accuracy is not confirmed, then the wire probe unit 10 is repositioned and the steps repeated until the desired confirmation is attained.

Assuming that such accuracy is not confirmed, a relocation of the probe wire is desirable in order to effect an optimum surgical result. In order to relocate wire 20, stabilizer 14 is moved to its retracted position shown in FIG. 2. The procedure is repeated until hook 22 of the probe wire 20 is properly located. Following confirmation by a mammography, stabilizer 14 is moved to its closed position and end 22 of probe wire 20 exits from needle 24 as illustrated in FIG. 1. Note that the freed wire tip 22 has assumed the shape of a relatively small curl or hook whereby the probe wire 20 anchors itself in the tissue at the lesion site. Once wire 20 has been finally located with confirmed accuracy, the needle cannula 12 and stabilizer 14 are taped to the patient to inhibit displacement of probe wire 20 upon subsequent body handling and transportation.

Since certain changes may be made in the foregoing disclosure without departing from the scope of the invention herein involved, it is intended that all matter contained in the above description and depicted in the accompanying drawings be construed in an illustrative and not in a limiting sense.

What is claimed:

1. A device for locking and positioning a probe wire for use with a straight, tubular cannula needle having a sharp point at a front end and a hub at a back end, wherein the hub has an open-ended longitudinal socket, the probe wire is slidably received in the cannula needle, and the probe wire has a J-shaped hook at its distal end which end assumes the straight configuration of the cannula needle when sheathed therein but assumes a hook configuration when pushed through the cannula needle, said device comprising:

(a) a clamp having a medial body, guide means and clamping means, said guide means longitudinally extending from a front end of said body, said clamping means longitudinally extending from a back end of said body, said clamping means having a frusto conical tip at its outer back end and a threaded portion at its inner front end, said guide means being sized and shaped to be received in the hub socket;

(b) a cap having a longitudinally disposed internal chamber that is open at a front end of said cap, said chamber having a frusto conical cavity at its inner back end and an internally threaded portion at its front end, wherein said frusto conical cavity is configured to matingly receive said frusto conical tip, and said internally threaded portion is configured to receive said threaded portion of said clamping means; and (c) said clamp and said cap each having a longitudinally-extending bore through which the probe wire is slidably received, said clamping means being designed (a) to permit the probe wire to slide in said bore when said cap is loosely threaded on said threaded portion of said clamping means and (b) to captively hold the probe wire when said cap is tightly threaded on said threaded portion of said clamping means.

2. The device as claimed in claim 1 wherein said guide means is a cylindrical member.

3. The device as claimed in claim 1 wherein said clamping means has four clamping fingers, adjacent ones of said clamping fingers being separated by a longitudinally-extending slot.

4. The device as claimed in claim 1 wherein said clamping means is a plurality of longitudinally disposed clamping fingers, adjacent ones of said clamping fingers being separated by a longitudinally extending slot.

5. The device as claimed in claim 4 wherein said clamping means is composed of polycarbonate.

6. The device as claimed in claim 4 wherein said frusto conical tip of said clamping means includes an inner cylindrical portion and a beveled outer portion, and said threaded portion is formed on said inner cylindrical portion.

7. The device as claimed in claim 5 wherein said guide means includes an inner cylindrical portion and a beveled outer portion, and said medial body portion includes a stop adjacent an innermost end of said inner cylindrical portion.

8. The device as claimed in claim 6 wherein said frusto conical cavity at said inner end of said chamber is designed to cooperate with said beveled outer portion of said clamping means to force said fingers inwardly against a probe wire received in said bore.

9. A probe unit adapted for marking the location of a lesion comprising:

(a) a tubular cannula needle adapted for insertion into a body to the site of a lesion, said cannula needle having a sharp point at one end and a hub with an open-ended socket at the other end;

(b) a probe wire adapted to closely fit and be freely slidable through said cannula needle;

(c) said probe wire possessing a memory hook at its distal end whereby such end assumes the configuration of said cannula needle when sheathed therein but assumes said hook configuration when pushed through said cannular needle to thereby anchor itself in tissue at the lesion when said cannula needle and probe wire therein has been inserted into the body at the lesion site; and (d) a stabilizer having a longitudinally extending bore that is sized and shaped to slidably receive said probe wire, said stabilizer including clamping means for captively holding said probe wire and fixing said stabilizer and probe wire against relative movement, wherein said stabilizer further includes:

(i) a clamp having a medial body, guide means and clamping means, said guide means longitudinally extending from a front end of said body, said clamping means longitudinally extending from a back end of said body, said clamping means having a frusto conical tip at its outer back end and a threaded portion at its inner front end, said guide means being sized and shaped to be received in said socket formed in said hub;

(ii) a cap having a longitudinally disposed internal chamber that is open at a front end of said cap, said chamber having a frusto conical cavity at its inner back end and a threaded portion at its front end, wherein said frusto conical cavity is configured to matingly receive said frusto conical tip of said clamping means; and (iii) said clamping means being designed (a) to permit said stabilizer to slide on said probe wire when said cap is loosely threaded on said clamp, and (b) to prevent said stabilizer from moving relative to said probe wire when said cap is tightly threaded on said clamp.

10. A probe unit adapted for marking the location of a lesion, and especially for marking the location of a presymptomatic, non-palpable breast lesion, comprising:

(a) a tubular cannula needle adapted for insertion into a body to the site of a lesion, said cannula needle having a sharp point at one end and a hub with an open ended socket at the other end;

(b) a probe wire adapted to closely fit and be freely slidable through said cannula needle;

(c) said probe wire possessing a memory hook at its distal end whereby such end assumes the configuration of said cannula needle when sheathed therein but assumes the hook configuration when pushed through said cannula needle to thereby anchor itself in the tissue at the lesion when said cannula needle and probe wire therein has been inserted into the body at about the lesion site;

(d) said probe wire possessing the further characteristic of a predetermined degree of soft flexibility whereby said wire is adapted to be manually actuated to release and easily slide from an anchored location to a fully sheathed position within the cannula without undue destruction of surrounding tissue;

(e) whereby the probe unit may be relocated within the body and the probe wire reanchored within the tissue until a desired accuracy is attained with respect to lesion location;

(f) a clamp having a medial body, guide means and clamping means, said guide means longitudinally extending from a front end of said body, said clamping means longitudinally extending from a back end of said body, said clamping means having a frusto conical tip at its outer back end and a threaded portion at its inner front end, said guide means being sized and shaped to be received in said socket in said hub;

(g) a cap having a longitudinally disposed internal chamber that is open at a front end of said cap, said chamber having a frusto conical cavity at its inner back end and a threaded section at its front end, said threaded section being designed to threadably engage said threaded portion of said clamping means and said frusto conical cavity being configured to matingly receive said frusto conical tip of said clamping means; and (h) said clamp and said cap each having a longitudinally-extending bore through which said probe wire is slidably received, said clamping means being designed (a) to permit said probe wire to slide in said bore when said cap is loosely threaded on said clamping means and (b) to captively hold said probe wire when said cap is tightly threaded on said clamping means.

11. A device for use in positioning and locking a probe wire relative to a cannula assembly comprising (a) a straight, tubular cannula needle having a central bore sized to slidably receive said probe wire and openings at its front and rear ends coupled with said bore and (b) a hub attached to said rear end of said needle, said hub having an open-ended socket which is coupled with said bore in said needle, said probe wire being slidably mounted in said central bore of said cannula needle, and said probe wire having a J-shaped hook at its distal end which assumes the straight configuration of the cannula needle when the distal end is received in the cannula needle but assumes its J-shaped hook configuration when not received in the cannula needle, said device comprising:

a body assembly comprising first and second body members and means for rotatably mounting said first body member to said second body member, said body assembly including an opening extending through said first and second body members, said opening being sized so that said probe wire may be slidably received therein, whereby said first and second body members may be caused to slide along the length of said probe wire;

clamp means coupled to said body assembly for releasably clamping said body assembly to said probe wire at a selected location along the length of said probe wire when said probe wire is received in said opening and said first body member is caused to rotate in a first direction about the long axis of said probe wire relative to said second body member; and stop means attached to said body assembly for coacting with said hub so as to prevent said body assembly from moving in a first direction relative to said hub.

12. A device according to claim 11 wherein said stop means comprises (a) a flat surface on one end of said second member and (b) an elongate member sized for receipt in said open-ended socket of said hub, said elongate member being attached to said one end of said second member.

13. A device according to claim 11 wherein said first member comprises a blind threaded bore having a frusto-conical cavity at its inner end and said second member has an elongate threaded portion sized to threadably engage said threaded bore and a frusto-conical tip portion configured to matingly engage said frusto-conical cavity.

14. A device according to claim 13 wherein said second member includes a longitudinally-extending slot positioned and configured to divide said frusto-conical tip portion into a plurality of elongate fingers.

* * * * *